US007691325B2

(12) United States Patent
Chopra et al.

(10) Patent No.: US 7,691,325 B2
(45) Date of Patent: Apr. 6, 2010

(54) PHOTONIC CRYSTAL SOLVENT VAPOR SENSING DEVICE

(75) Inventors: Naveen Chopra, Oakville (CA); Peter M. Kazmaier, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 538 days.

(21) Appl. No.: 11/551,090

(22) Filed: Oct. 19, 2006

(65) Prior Publication Data

US 2008/0095664 A1 Apr. 24, 2008

(51) Int. Cl.
*G01N 31/22* (2006.01)
*C09K 19/00* (2006.01)

(52) U.S. Cl. .............................. 422/58; 422/55; 422/50; 428/1.26; 428/1.2; 428/1.1

(58) Field of Classification Search .................. 422/58, 422/50; 428/1.26, 1.2, 1.1; 521/54
See application file for complete search history.

(56) References Cited

U.S. PATENT DOCUMENTS

| | | | | |
|---|---|---|---|---|
| 6,014,246 | A | 1/2000 | Asher et al. | |
| 6,094,273 | A | 7/2000 | Asher et al. | |
| 6,165,389 | A | 12/2000 | Asher et al. | |
| 6,235,801 | B1 * | 5/2001 | Morales et al. | 521/54 |
| 2004/0131799 | A1 | 7/2004 | Arsenault et al. | |

OTHER PUBLICATIONS

Cho et al., Connected Open Structures from Close-Packed Colloidal Crystals by Hyperthermal Neutral Beam Etching, 2005, Langmuir, 21, 10770-10775.*

Arsenault et al., Vapor swellable colloidal photonic crystals with pressure tunability, 2005, J. Mater. Chem., 15, 133-138.*

Kulbaba, K. et al., Organometallic Gels: Characterization and Electrochemical Studies of Swellable, Thermally Crosslined Poly(ferrocenylsilane)s, Macromol. Chem. Phys., 2001, 202, 1768-1775.*

MacLachlan M. et al, Spirocyclic [1] Rerrocenophanes: Novel Cross-Linking Agents for Ring-Opened Poly(ferrocenes), Macromolecules, 1996, vol. 29, No. 26.*

Arsenault, et al., "A Polychromic, Fast Response Metallopolymer Gel Photonic Crystal With Solvent and Redox Tunability: A Step Towards Photonic Ink (P-Ink)", Advanced Materials, Mar. 17, 2003, vol. 15, No. 6, pp. 503-507.

Foulger, et al., "Photonic Bandgap Composites", Advanced Materials, Dec. 17, 2001, vol. 13, No. 24, pp. 1898-1901.

Fudouzi, et al., "Photonic Papers and Inks: Color Writing With Colorless Materials", Advanced Materials, Jun. 5, 2003, vol. 15, No. 11, pp. 892-896.

Holtz, et al., "Polymerized Colloidal Crystal Hydrogel Films as Intelligent Chemical Sensing Materials", Nature, Oct. 23, 1997, vol. 389, Macmillan Publishers Ltd., pp. 829-832.

Weissman, et al., "Thermally Switchable Periodicities and Diffraction from Mesoscopically Ordered Materials", Science, Nov. 8, 1996, vol. 724, pp. 959-960.

Takeoka, et al., "Polymer Gels That Memorize Structures of Mesoscopically Sized Templates. Dynamic and Optical Nature of Periodic Ordered Mesoporous Chemical Gels", Langmuir, 2002, American Chemical Society, published on web Jun. 29, 2002, pp. 5977-5980.

Fudouzi, et al., "Colloidal Crystals with Tunable Colors and Their Use as Photonic Papers", Langmuir, 2003, American Chemical Society, published on web Sep. 30, 2003, pp. 9653-9660.

* cited by examiner

*Primary Examiner*—Walter D Griffin
*Assistant Examiner*—Christine T Mui
(74) *Attorney, Agent, or Firm*—Oliff & Berridge, PLC

(57) ABSTRACT

A method of manufacturing a vapor-sensing device, including placing an aqueous dispersion of colloidal spheres on a substrate, drying the aqueous dispersion of colloidal spheres to obtain a colloidal crystal, filling the voids among the colloidal crystal with a vapor-expandable matrix composition, curing the vapor-expandable matrix composition, and peeling away any excess vapor-expandable matrix material from the surface of the film, so that the colloidal crystal is exposed.

17 Claims, No Drawings

PHOTONIC CRYSTAL SOLVENT VAPOR SENSING DEVICE

TECHNICAL FIELD

This disclosure is generally directed to vapor sensing devices and, in particular, to photonic crystal films used to detect solvent vapors. This disclosure also relates to methods of making and using such vapor sensing devices and films.

BACKGROUND

Typical vapor sensor devices, such as those that are used to determine $O_2$ gas levels and breathalyzer units for alcohol measurement rely on complex chemical processes that make the devices costly. For example, breathalyzer units rely on chemical reactions, infrared radiation analysis, or fuel cells to measure blood alcohol content. Such devices are relatively complex, and can be expensive. There exists a need for a low-cost simple alternative sensing unit for the detection of various solvent vapors.

SUMMARY

This disclosure describes the fabrication and use of a thin film device that can be used to visually detect the presence of solvent vapors. The sensor in embodiments can be a composite film made of an ordered array of monodisperse colloidal-sized spheres embedded within a vapor-expandable matrix. Due to small interparticle distances between the spheres, the film exhibits Bragg diffraction of visible light, giving an iridescent opal-like appearance. There is an easily observable, rapid, and reversible color change in the presence of a solvent vapor due to swelling of the matrix and the concomittal modulation of the Bragg diffraction wavelength.

In an embodiment, the present disclosure provides a method of manufacturing a vapor-sensing device, comprising placing an aqueous dispersion of colloidal spheres on a substrate, drying the aqueous dispersion of colloidal spheres to obtain a colloidal crystal, filling the voids among the colloidal crystal with a vapor-expandable matrix composition, curing the vapor-expandable matrix composition, and peeling away any excess vapor-expandable matrix material from the surface of the film, so that the colloidal crystal is exposed.

In an embodiment, the present disclosure provides a vapor-sensing device, comprising a vapor-expandable matrix, and a colloidal crystal embedded within the vapor-expandable matrix, wherein the vapor-expandable matrix comprises a composition that reversibly swells in the presence of at least one type of vapor, the colloidal crystal exhibits Bragg diffraction, and at least one surface of the colloidal crystal is exposed directly to the environment.

In an embodiment, the present disclosure provides a vapor monitor badge, comprising a substrate, a vapor-expandable matrix secured to the substrate, and a colloidal crystal embedded within the vapor-expandable matrix, wherein the vapor-expandable matrix comprises a composition that reversibly swells in the presence of at least one type of vapor, the colloidal crystal exhibits Bragg diffraction, and at least one surface of the colloidal crystal is exposed directly to the environment.

EMBODIMENTS

Vapor sensing devices will now be described comprising a vapor-expandable matrix and an ordered array of monodisperse colloidal-sized spheres embedded within the vapor-expandable matrix. Also described herein are methods of making and using vapor sensing devices according to embodiments of the invention.

A vapor-expandable matrix may be composed of any material that will positively interact with a vapor type to be detected. The term “interact” means that the vapor is capable of diffusing into the vapor-expandable matrix and causes the vapor-expandable matrix to swell or expand. Further, in embodiments, the interaction between the vapor or vapors to be detected and the vapor-expandable matrix can be reversible, as the relative concentration of the vapor or vapors changes. Thus, for example, an interaction between a particular vapor and the vapor-expandable matrix can cause the vapor-expandable matrix to expand as the vapor concentration increases, and contract as the vapor concentration decreases.

In embodiments, this interaction is related to a detectable change in the sensor characteristics. For example, the interaction can cause a visible color of the sensor to change from a first color to a second color, as the vapor-expandable matrix changes from one state of vapor expansion to a second state of vapor expansion. This color change, which can be directly or indirectly related to a concentration of vapor present in the vapor-expandable matrix, can thus be correlated to the vapor concentration.

Embedded in the vapor-expandable matrix is a three-dimensional crystal lattice of monodispersed colloidal-sized spheres. The colloidal spheres selected must be able to monodisperse in an array that exhibits Bragg diffraction. Additionally, the colloidal spheres need to be composed of a material that is insoluble in the vapor type to be detected.

The initial color of the sensor is dependent in part on the size of the colloidal spheres selected. In order to obtain an initial color that is within the visible spectrum, the diameter of the colloidal spheres should have an average particle size, or diameter, of from about 100 to about 300 nm, such as about 150 to about 260 nm. Of course, if color change detection is to be by other than visible light, such as by a change in infrared or ultraviolet light, then smaller or larger sized particles can be used. However, it may be desirable to have sphere diameters outside this range. Additionally, it may be desirable that the initial color of the sensor would be clear, which requires selection of colloidal spheres having an average particle size corresponding to a Bragg’s diffraction peak on the smaller wavelength side outside of the visible spectrum. Other parameters may be set so that the presence of the desired vapor-type turns the clear sensor to a visible color.

When the sensor is exposed to a solvent vapor, the vapor-expandable matrix swells, and the interparticle distances are increased (from $d_1$ to $d_2$). The result is a shift in the Bragg diffraction peak and a change in color. If the shift in the Bragg diffraction peak is large enough, the change in color can be detected by the naked eye. When the film is removed from the solvent vapor environment, the film shrinks back to its original shape and color. Of course, vapor presence and concentration can be determined other than by color measurement by the naked eye. For example, the sensor can be attached to or arranged near a color detection device that more precisely determines the color of the sensor, provides more accurate measurements, or to measure smaller color changes. Other measurement devices can also be used to measure color change of the vapor-expandable matrix.

The degree of crosslinking in the vapor-expandable matrix and the nature of the solvent both play a role in the degree of swelling of the matrix and thus the shift in the Bragg diffraction peak. In general, vapors of compounds having smaller molecules or low molecular weight will swell the matrix more so than the vapors of compounds having larger molecules and higher molecular weights. To ensure maximum swelling response, the degree of crosslinking is desired less than about 5%. However, if the degree of crosslinking is below about 2%, the film of the sensor can be very tacky and soft, and is not as mechanically stable. A suitable range for crosslinking density could thus be from about 2% to about 5%, such as about 2 to about 2.5%, or about 2.5 to about 4%.

Some matrix compositions are better suited than other matrix compositions for detecting certain types of vapors. For example, while polydimethylsiloxane (PDMS) interacts strongly with volatile oil vapors or organic solvent vapors, PDMS does not interact strongly with water vapor. However, hydrogels interact strongly with water vapor.

For the detection of volatile oil vapors, suitable matrix compositions include silicone rubber (including polydimethylsiloxanes) and other elastomeric polymers, such as polybutadiene (including styrene-butadiene rubber—a copolymer of styrene and butadiene, and nitrile rubber—a copolymer of polybutadiene and acrylonitrile), polyisoprene (including butyl rubber-copolymer of isobutylene and isoprene, and halogenated butyl rubbers), and chloroprene rubber (commercially known as Neoprene).

For the detection of organic solvent vapors, suitable matrix compositions include silicone rubber (including polydimethylsiloxanes) and other elastomeric polymers, such as polybutadiene (including styrene-butadiene rubber—a copolymer of styrene and butadiene, and nitrile rubber—a copolymer of polybutadiene and acrylonitrile), polyisoprene (including butyl rubber-copolymer of isobutylene and isoprene, and halogenated butyl rubbers), and chloroprene rubber. Some elastomer compositions may be better suited for certain solvents. For example, polar elastomer matrices may be better suited for the detection of certain polar solvents and non-polar matrices may be better suited for the detection of certain non-polar solvents.

For the detection of water vapors, suitable matrix compositions include water compatible polymers, such as NIPAM (N-isopropyl acrylamide), PVA (polyvinyl alcohol), PEO (polyethylene oxide), and PEG (polyethylene glycol). To avoid complete dissolution of these matrices, the polymer may be crosslinked.

Likewise, certain colloidal sphere materials are better suited than others for the detection of certain types of vapors. For example, while polystyrene spheres work well for detecting volatile oil vapors, they do not work well for detecting organic solvent vapors, as polystyrene dissolves in the presence of organic solvents. However, silica spheres do not dissolve in the presence of organic solvent vapors, and are thus better suited for such an application.

For the detection of volatile oil vapors, the colloidal spheres may be composed of either organic materials or inorganic materials. Suitable organic materials may include polystyrene and PMMA (polymethyl methacrylate). Suitable inorganic materials may include glass beads, silica spheres, titania spheres, and zirconia spheres.

For the detection of organic solvent vapors, the colloidal spheres should be composed of an inorganic material, including glass beads, silica spheres, titania spheres, and zirconia spheres.

For the detection of water vapor, the colloidal spheres may be composed of polystyrene, PMMA, glass beads, silica spheres, titania spheres, and zirconia spheres.

Accordingly, the present disclosure is directed to vapor sensing devices generally comprising combinations of the above-described vapor-expandable matrix and an ordered array of monodisperse colloidal-sized spheres embedded within the vapor-expandable matrix. Although some selection of particular vapor-expandable matrix and colloidal-sized spheres may be necessary depending on the particular vapors to be detected, such selection can be readily made based, for example, on the polarity of the vapor, the relative size of the vapor molecules, the interaction of the vapor molecules with various matrix and spheres materials, and the like.

In addition, various modifications of the vapor sensing device materials may be made, to achieve different results. For example, if desired, the matrix and spheres materials may be selected in combination with desired vapors to be detected, such that the vapor molecules penetrate the vapor sensing device at different rates. For example, if the materials are selected such that the vapor molecules penetrate the device at a slower rate, then the color change of the device will be slower when exposed to the vapor molecules. However, because the vapor molecules will dissociate out of the device at the same slow rate when the vapor concentration is reduced, the color change of the device back to its original state will be slower, thus allowing for longer visualization of the color change.

Alternatively, if desired, the matrix and spheres materials may be selected in combination with desired vapors to be detected, such that the vapor molecules quickly penetrate the vapor sensing device. In this embodiment, the color change of the device will be faster, and nearly instantaneous, when exposed to the vapor molecules. This faster color change will allow, for example, electronic detection of color change to provide a much faster indication of vapor presence when visual inspection may not be as reliable or when slower detection is disadvantageous. Also, as above, because the vapor molecules will dissociate out of the device at the same faster rate when the vapor concentration is reduced, the color change of the device back to its original state will be faster.

In other embodiments, the matrix material can be modified to trap vapor molecules that dissociate into the matrix. For example, the matrix may include a material that binds to the vapor molecules, to trap those vapor molecules in the matrix and prevent reverse dissociation. For example, a binding substance can be applied to the surface of the spheres, or incorporated into the matrix itself, which would bind the vapor molecules to trap them in the matrix. Alternatively, the matrix and/or sphere materials may be modified such that the vapor molecules cause curing or cross-linking with the matrix and/or sphere materials, to trap the vapor molecules and freeze the swelling of the matrix. This would provide a vapor sensing device that exhibits a permanent color change, such as by a permanent matrix swelling, upon exposure to the desired vapor molecules.

A method of manufacturing a vapor-sensing device includes placing an aqueous dispersion of colloidal spheres on a substrate, drying the aqueous dispersion of colloidal spheres to obtain a colloidal crystal, filling the voids among the colloidal crystal with a vapor-expandable matrix composition, curing the vapor-expandable matrix composition, and peeling the excess vapor-expandable matrix material from the surface of the film.

As a substrate, a number of materials may be used, including glass, plastics, mylar films, metal foils, silicon wafers, and mica. The substrate may be rigid or flexible. The surface of the substrate should be free from any contaminants that may interfere with the structuring of the colloidal crystal. Additionally, a hydrophilic substrate surface ensures greater adhesion of the colloidal spheres and facilitates the self-assembly of the spheres into a close-packed array.

After placing the aqueous dispersion of the colloidal spheres on the substrate, the colloidal spheres may be coated with a viscous material to retard the rate of evaporation of the aqueous media, thus increasing the drying time. The drying time needs to be long enough to allow the spheres to come together in a close-packed array.

Before filling the voids among the colloidal crystal with a vapor-expandable matrix composition, the vapor-expandable matrix composition may be combined with a diluent. The diluent helps the penetration of the vapor-expandable matrix composition into the void spaces between the spheres. Lower viscosity fluids will better aid in reducing the viscosity than higher viscosity fluids. Thus, in embodiments, the viscosity of the fluid should be less than about 20 cst. Any diluent that does not dissolve the colloidal spheres, and is miscible with the vapor-expandable matrix composition would be suitable.

Suitable diluents for use with organic polymer matrix/organic spheres include low molecular weight silicone fluids and hydrocarbon solvents that do not dissolve the spheres.

Suitable diluents for use with organic polymer matrix/inorganic spheres include silicone fluids and organic solvents.

Suitable diluents for use with water miscible matrix/organic spheres include water and water miscible organic solvents, such as MeOH, EtOH, and acetone.

Suitable diluents for use with water miscible matrix/inorganic spheres include water and water miscible organic solvents, such as MeOH, EtOH, and acetone.

It was unexpectedly discovered that peeling the excess vapor-expandable matrix material from the surface of the film provides a vapor-sensing device that shows a greater degree of swelling and a faster response time in the presence of vapor than when the excess matrix material is not removed. This result is believed to be due to the fact that when the excess vapor-expandable matrix material is peeled away from the surface of the film, it exposes the colloidal crystal.

As discussed above, embodiments of the vapor-sensing device may be configured to allow detection of the presence of a vapor type by observing a color change of the vapor-sensing device with the naked eye. The color change may be easily detectable by observing with the naked eye a change of one visible color to another, such as from green to red, or a change from clear to a visible color, or a change from a visible color to clear.

One embodiment of the vapor-sensing device is a vapor monitor badge comprising a vapor-expandable matrix and an ordered array of monodisperse colloidal-sized spheres embedded within the vapor-expandable matrix secured to a substrate. The vapor monitor badge may be configured to allow the monitor badge to be secured to an article of clothing, or to be secured to one's person by a string or a chain, or some similar device. The size and shape of the badge and the composition of the substrate need not be limited. Additionally, a vapor monitor badge may also be configured to be secured to a vertical surface, such as a wall, window, or a door. Or, the monitor badge may be configured to allow it to be placed on a horizontal surface such as a table, bench, or floor, or to hang it from or secure it to an overhead surface such as a ceiling.

However, embodiments of the vapor-sensing device may be configured to allow detection of the presence of a vapor type with various types of instruments. The use of such instruments may allow the detection of smaller amounts of vapors, or for certain types of vapors that do not interact strongly enough with the matrix to detect with the naked eye. Instruments may also be used to quantify the amount or concentration of a vapor.

The use of UV/visible absorbance spectroscopy is a useful tool to monitor the wavelength of reflected light. Independently, one would measure the solvent vapor concentration using a sensor device. Using this data, a colorimetric calibration curve may be generated that would allow one to estimate the solvent vapor concentration by the absorbance wavelength, essentially a visual tool to monitor the solvent vapor concentration. Other ways of monitoring solvent vapors in a closed system, such as a room, include diffusion detector tubes, vapor monitor badges, personal air sampling pumps, detector tubes and pumps, hand-held electronic monitors, and fixed air monitors.

EXAMPLE

An aqueous latex dispersion of 202 nm polystyrene spheres (Polysciences) was dispensed onto plasma etched glass microscope slides, and overcoated with 10 cSt silicone fluid. The coatings were allowed to stand overnight at room temperature then heated to 55° C. to complete the evaporation of water/self-assembly of the opal lattice. Next, the silicone fluid was washed away with isopropyl alcohol, taking care not to scratch away the opal film. A mixture of 1:1 Sylgard 184 (containing 5 wt % curing agent):0.65 cSt silicone fluid was prepared and overcoated onto the opal film. This was allowed to stand overnight at room temperature, then the curing was completed by heating film for 8 h at 55° C. After curing, the excess PDMS was peeled away from the surface of the film.

It will be appreciated that the various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method of manufacturing a vapor-sensing device, comprising:

placing an aqueous dispersion of colloidal spheres on a substrate;

drying the aqueous dispersion of colloidal spheres to obtain a colloidal crystal;

filling the voids among the colloidal crystal with a crosslinked vapor-expandable matrix composition having a 2% to 5% crosslinking density;

curing the vapor-expandable matrix composition; and peeling away any excess vapor-expandable matrix material from the surface of the film, wherein the colloidal crystal is exposed wherein:

the vapor-expandable matrix comprises a composition that reversibly swells in the presence of at least one type of vapor, the composition selected from the group consisting of:

hydrogels, polydimethylsiloxane (PDMS), styrene-butadiene rubbers, nitrile rubbers, butyl rubbers, halogenated butyl rubbers, chloroprene rubbers, N-isopropyl acrylamides (NIPAMs), polyvinyl alcohols (PVAs), polyethylene oxides (PEOs), and polyethylene glycols (PEGs);

the colloidal crystal exhibits Bragg diffraction; and at least one surface of the colloidal crystal is exposed directly to the environment.

2. The method according to claim 1, wherein the vapor expandable matrix composition comprises polydimethylsiloxane (PDMS).

3. The method according to claim 1, wherein the vapor expandable matrix composition comprises a hydrogel.

4. The method according to claim 1, wherein the colloidal spheres comprises polystyrene.

5. The method according to claim 1, wherein the colloidal spheres comprises silica.

6. The method according to claim 1, wherein the colloidal spheres comprises titania.

7. The method according to claim 1, wherein a diameter of the colloidal spheres is from about 150 nm to about 260 nm.

8. The method according to claim 1, wherein the crosslinked vapor-expandable matrix composition has a crosslinking density of from about 2% to about 2.5%.

9. A vapor-sensing device, comprising:

a crosslinked vapor-expandable matrix having a 2% to 5% crosslinking density; and a colloidal crystal comprising colloidal spheres embedded within the vapor-expandable matrix;

wherein:

the vapor-expandable matrix comprises a composition that reversibly swells in the presence of at least one type of vapor, the composition selected from the group consisting of:

hydrogels, polydimethylsiloxane (PDMS), styrene-butadiene rubbers, nitrile rubbers, butyl rubbers, halogenated butyl rubbers, chloroprene rubbers, N-isopropyl acrylamides (NIPAMs), polyvinyl alcohols (PVAs), polyethylene oxides (PEOs), and polyethylene glycols (PEGs);

the colloidal crystal exhibits Bragg diffraction; and at least one surface of the colloidal crystal is exposed directly to the environment.

10. The device according to claim 9, wherein an average diameter of the colloidal spheres is from about 150 nm to about 260 nm.

11. The device according to claim 9, wherein the degree of crosslinking is from 2% to about 2.5%.

12. A method of detecting the presence of a vapor, comprising:

exposing the vapor-sensing device according to claim 9, to the vapor, wherein the vapor swells the vapor-expandable matrix of the vapor-sensing device; and observing a shift in a Bragg-diffraction peak of the vapor-sensing device.

13. The method according to claim 12, wherein the step of observing a shift in a Bragg-diffraction peak of the vapor-sensing device includes quantifying a shift in a Bragg-diffraction peak to obtain a value, and correlating the value to a vapor concentration.

14. A vapor monitor badge, comprising:

a substrate;

a crosslinked vapor-expandable matrix having a 2% to 5% crosslinking density secured to the substrate; and a colloidal crystal comprising colloidal spheres embedded within the vapor-expandable matrix;

wherein:

the vapor-expandable matrix comprises a composition that reversibly swells in the presence of at least one type of vapor, the composition selected from the group consisting of:

hydrogels, polydimethylsiloxane (PDMS), styrene-butadiene rubbers, nitrile rubbers, butyl rubbers, halogenated butyl rubbers, chloroprene rubbers, N-isopropyl acrylamides (NIPAMs), polyvinyl alcohols (PVAs), polyethylene oxides (PEOs), and polyethylene glycols (PEGs);

the colloidal crystal exhibits Bragg diffraction; and at least one surface of the colloidal crystal is exposed directly to the environment.

15. The device according to claim 9, wherein:

the vapor-expandable matrix comprises a composition that reversibly swells in the presence of volatile oil vapor, the composition selected from the group consisting of polydimethylsiloxane (PDMS), styrene-butadiene rubbers, nitrile rubbers, butyl rubbers, halogenated butyl rubbers, and chloroprene rubbers;

the colloidal spheres are composed of a material selected from the group consisting of polystyrene, polymethyl methacrylate (PMMA), glass beads, silica spheres, titania spheres, and zirconia spheres; and the device is configured to exhibit a detectable shift in a Bragg diffraction peak in the presence of volatile oil vapor.

16. The device according to claim 9, wherein:

the vapor-expandable matrix comprises a composition that reversibly swells in the presence of organic solvent vapor, the composition selected from the group consisting of polydimethylsiloxane (PDMS), styrene-butadiene rubbers, nitrile rubbers, butyl rubbers, halogenated butyl rubbers, and chloroprene rubbers;

the colloidal spheres are composed of a material selected from the group consisting of glass beads, silica spheres, titania spheres, and zirconia spheres; and the device is configured to exhibit a detectable shift in a Bragg diffraction peak in the presence of organic solvent vapor.

17. The device according to claim 9, wherein:

the vapor-expandable matrix comprises a composition that reversibly swells in the presence of water vapor, the composition selected from the group consisting of N-isopropyl acrylamides (NIPAMs), polyvinyl alcohols (PVAs), polyethylene oxides (PEOs), and polyethylene glycols (PEGs);

the colloidal spheres are composed of a material selected from the group consisting of polystyrene, polymethyl methacrylate (PMMA), glass beads, silica spheres, titania spheres, and zirconia spheres; and the device is configured to exhibit a detectable shift in a Bragg diffraction peak in the presence of water vapor.

* * * * *